United States Patent [19]

Hussain et al.

[11] Patent Number: 4,552,693

[45] Date of Patent: Nov. 12, 1985

[54] TRANSPARENT FRAGRANCE EMITTING ARTICLES

[75] Inventors: Zahera J. Hussain, Wyckoff, N.J.; Ronald D. Zukoski, Warwick, N.Y.

[73] Assignee: Avon Products, Inc., New York, N.Y.

[21] Appl. No.: 480,501

[22] Filed: Mar. 30, 1983
(Under 37 CFR 1.47)

[51] Int. Cl.$^4$ ............................ A61K 7/46; C11B 9/00
[52] U.S. Cl. .................................................. 252/522 A
[58] Field of Search ..................................... 252/522 A

[56] References Cited

U.S. PATENT DOCUMENTS

| | | | |
|---|---|---|---|
| 3,567,119 | 3/1971 | Wilbert et al. | 252/522 A |
| 3,725,311 | 4/1973 | Grubb | 252/522 A |
| 3,926,655 | 12/1975 | Miles | 252/522 A |
| 4,051,159 | 9/1977 | Tsoucalas et al. | 252/522 A |
| 4,110,261 | 8/1978 | Newland | 424/76 |
| 4,125,478 | 11/1978 | Sullivan et al. | 252/522 A |
| 4,136,250 | 1/1979 | Mueller et al. | 252/522 A |
| 4,356,115 | 10/1982 | Shibanai et al. | 252/522 A |
| 4,405,509 | 9/1983 | Rogers et al. | 252/522 A |
| 4,409,201 | 10/1983 | Heinrich et al. | 252/522 A |

*Primary Examiner*—Helen M. S. Sneed

[57] ABSTRACT

Transparent fragrance-emitting articles, formed from a composition which has a relatively low set point and comprises a thermoplastic polyamide resin plasticizer system, are disclosed. The plasticizer system comprises a sulfonamide and mineral oil which have been titrated to clarity with a solvent for both the oil and sulfonamide. A fragrance-emitting article may be made by blending the polyamide with the plasticizer system, adding fragrance to the blend while at a temperature below 120° C. and then rotational or shell molding to form the fragrance-emitting article.

17 Claims, No Drawings

4,552,693

TRANSPARENT FRAGRANCE EMITTING ARTICLES

BACKGROUND OF THE INVENTION (a) Field of the Invention

This invention relates to solid transparent fragrance-emitting articles. The articles can be three dimensional self-supporting figures formed by rotational, solid or shell molding techniques.

(b) State of the Art

Transparent or clear fragrance-emitting articles are aesthetically more appealing than those which are opaque.

In general, fragrance loss during processing has been a problem in manufacture of solid transparent fragrance-emitting articles and has limited the means by which such articles can be formed. Also, rotational and shell molding techniques which entail substantial processing periods have generally been unsatisfactory for use in manufacture of fragrance emitting articles due to loss of fragrance oils by vaporization particularly when using polymers having high set temperatures. Polymer materials, which have higher temperature set points necessitating higher processing temperatures, are particularly unsuitable as base materials for fragrance-emitting articles, since fragrance loss increases with increased temperature.

U.S. Pat. No. 3,926,655 describes clear cosolvent free polyamide resin articles containing up to 30% perfume oil. Solid objects are made by melting resins having a molecular weight of 6000 to 9000, adding perfume and rapidly cooling, as by quenching in cold water. The product can be molded under heat and pressure to the desired shape. The patent recomends use of closed, pressure vessels during mixing to avoid loss of fragrance oil by vaporization. When the final objects are injection molded (which is effected at high temperatures), it is preferred that the fragrance oil be introduced directly into the resin feed.

Other polymeric materials are unsuitable for use in fragrance-emitting articles because of problems with exudation of cosolvents for the fragrance and polymer or of other materials present in the article. U.S. Pat. No. 4,110,261 refers to a prior art polyamide resin for use in fragrance emitting objects having good gloss and transparency characteristics, but which becomes tacky to touch upon aging. U.S. Pat. No. 3,819,342 describes transparent candles formed from certain thermoplastic polyamide resins and a flammable solvent selected from the group consisting of saturated and unsaturated fatty alcohols, unsaturated fatty acids, esters of fatty acids with polyhydric alcohols and glycerol and mixtures thereof. The solvent is present in an amount sufficient to gel the resin. The candles may also include a fragrance which is emitted upon burning. Mineral oil may be used as an antiflaring agent. These compositions generally produce a relatively soft product which requires a support vessel and which is subject to syneresis.

U.S. Pat. No. 4,051,159 describes shaped, self-supporting transparent fragrance emitting articles formed from polyamide resin having a molecular weight of 2,000 to 10,000, a $C_{14}$ to $C_{22}$ alkyl alcohol as solvent and a fragrance emitting material. The polyamide may be formed from $C_{16}$ to $C_{22}$ linear fatty acids, such as linoleic acid and a di- /or polyamine, such as diethylene triamine and ethylene diamine. According to the patent, the materials are blended at 150° to 200° F. Optionally up to 15% mineral oil may be added to the composition to facilitate production of a homogenous mixture.

The present invention provides a composition, the set point of which is relatively low, resulting in reduced fragrance loss, thus permitting manufacture of three dimensional figures by rotational or shell molding. The plasticizer/solvent system of the composition imparts improved long-range stability to the fragranced products. The fragrance-emitting articles of the invention are stable during storage and use and do not suffer from syneresis, tackiness, softening or loss of shape.

SUMMARY OF THE INVENTION

This invention relates to a composition for forming a solid transparent fragrance-emitting article comprising a mixture of (a) a thermoplastic polyamide resin having a weight average molecular weight of 5,000 to 15,000 which is formed by reaction of a polycarboxylic acid of the formula $R(COOH)_x$ wherein R is a hydrocarbon group having 20 to 44 carbons and x is 2 or more, with a polyamine;

(b) a clear plasticizer/solvent system comprising a sulfonamide plasticizer, a gellant and a cosolvent for the plasticizer and the gellant, the solubility parameter of the polyamide resin and plasticizer/solvent system being compatible; and (c) a fragrance oil.

In preferred practice, the composition comprises 60 to 65 weight percent of a polyamide resin having a weight average molecular weight of 5,000–15,000 formed by reaction of linoleic acid dimer and diethylene triamine; 20 to 30 weight percent of a clear plasticizer system comprising 1 part by weight N-ethyl,o-,p-toluene sulphonamide, 2 parts by weight light viscosity mineral oil and nonyl phenol ethoxylate (1.5 moles EO) in an amount sufficient to make the system clear; and a fragrance oil in an amount equal to no more than 15 weight percent of the compositions. The composition is formed into a solid transparent fragrance-emitting article by mixing the polyamide resin and the plasticizer/solvent system, generally at a temperature above 120° C., cooling to a temperature above the mixture's set point but below about 120° C., adding up to 15 weight percent fragrance oil and molding the resulting product, preferably by rotational or shell molding.

DETAILED DESCRIPTION OF THE INVENTION

This invention provides compositions which can be molded into solid, self supporting fragrance-emitting articles which are clear, stable and nontacky. The unique solvent system resin composition employed in the invention sets at a relatively low temperature. Therefore, the articles can be molded at relatively low temperatures. The reduced processing temperature minimizes fragrance losses due to evaporation and substantially eliminates hazing and discoloration which can occur when gels containing fragrance oils are exposed to elevated temperatures particularly for extended periods. Because of these advantages of the present compositions, fragrance-emitting transparent articles can be rotational, solid or shell molded into essentially any desired shape.

The composition of the invention comprises (a) a thermoplastic polyamide resin, (b) a plasticizer/solvent system containing a plasticizer, a gellant and a cosolvent for the plasticizer and gellant, and (c) a fragrance oil.

The plasticizer/solvent system and the resin are mixed at a temperature at which the admixture is fluid. The mixture is then cooled to a temperature above the mixture's set point but below about 120° C. at which point the fragrance oil is added. Following fragrance addition a deformation resistant, fragrance-emitting article having good clarity may be formed by molding.

The compositions are easily processed and require no special handling for mixing or to minimize fragrance loss. The resulting article is stable in that exudation of solvent or syneresis does not become a problem during storage or use. The articles also exhibit good fragrance lift.

The thermoplastic polyamide resins which are useful in the practice of the invention are formed by condensation of a polycarboxylic acid and a polyamine. The acid has the formula $R(COOH)_x$ wherein R is a saturated or unsaturated hydrocarbon group containing twenty to forty-four carbons and x is at least 2. Acids having chains containing fewer than twenty carbons may exhibit solubility resistance in the composition of the invention. With carbon chains which are too long the product produced may be hazy, soft or subject to syneresis. The acids useful in the invention include fatty acids and their dimers. An acid which has been found particularly suitable in the practice of the present invention is the linoleic acid dimer for which R contains 34 carbons and x is 2. The polyamine typically is an alkylene polyamine. Preferred polyamines are ethylene polyamines, such as diethyl-enetriamine and ethylenediamine.

Polyamide resins which have a weight average molecular weight of 5,000 to 15,000, a viscosity at 190° C. of 5-100 poise and a softening point of 100° to 200° C. are preferred for use in the present invention. High molecular weight polyamides (i.e., >15,000) should be used only in combination with low molecular weight resins to produce an overall combination of resins within the molecular weight range specified above. The resins must be compatible with the plasticizer/solvent system. The polyamide employed should therefore be one whose solubility parameter is comparable to that of the plasticizer/solvent system. Generally a solubility parameter of 8-12.5 is required. Aromatic polyamides, nylons, high molecular weight polyamides based on pure dibasic acids with short repeating units, and polyesteramides generally are not compatible with the plasticizer/solvent system of the invention.

Among resins which have been used successfully in the invention are:

1. Unirez 2931 (Union Camp) which is based on a mixture unsaturated fatty acid dimers (linoleic/oleic acids) and a mixture of polyamines (ethylene diamine, diethylene triamine, hexamethylene tetramine etc.) having a weight average molecular weight of 12,000, a viscosity at 160° C. of 2,800-3,400 cps. and a solubility parameter (calculated from the solvent system used) of 8-10, preferably about 9.5;

2. Emerez 1590 based on similar acid/amine system as above having a low molecular weight range of less than 4000 and a viscosity at 160° C. of 400 cps;

3. Henkel BC 1231 which is based on a mixture of fatty acid dimers/dibasic acid and a polyamine and has a molecular weight range of 4,000-8,000, a viscosity of hot melt at 160° C. of 16,000-18,000 cps, and a solubility parameter in the range of 10.2-12.2.

The plasticizer/solvent system comprises a gellant, a plasticizer and a cosolvent. The plasticizer, as previously stated, must have a solubility parameter which is comparable to that of the polyamide resin employed.

The plasticizer is a sulfonamide. Generally pure sulfonamides rather than blends of sulfonamides with other materials should be employed in the practice of the invention. This limitation is due to the fact that some sulfonamide blends contain materials which can affect the transparency of the final fragrance-emitting article. As a class toluene sulfonamides of molecular weight 199.0 are suitable in the practice of the invention. N-ethyl,o-,p-toluene sulphonamide sold under the name Santicizer 8 (Monsanto) is effective for purposes of the invention. Its solubility parameter is 14.4. Other examples of plasticizers that are believed to be suitable include N-ethyl, N-isopropyl and N-butyl benzene sulfonamides and mixtures thereof.

The gellant used in the plasticizer system is preferably light viscosity mineral oil having a solubility parameter of 7.0-8.0. Other grades of mineral oil can also be used.

The cosolvent is commonly a long chain alkyl phenol ethoxylate. The alkyl chain length can be varied from 9 to 18 and the degree of ethoxylation can be between 1 to 3 moles EO. Higher ethoxylation reduces polyamide solubility in the system. A preferred cosolvent is nonyl phenolethoxylate (1.5 moles EO). Nonoxynol 2 sold under the name Igepal CO210 (GAF) is the cosolvent of choice. This material has a solubility parameter of 8.5. Other specific examples of suitable cosolvents are dinonylphenol ethoxylate (7.0 EO) sold under the name Igepal DM 430.

The plasticizer and gellant are preferably used in about a 1:2 weight ratio; that is, about twice as much gellant as plasticizer is employed in the plasticizer/solvent system. The cosolvent is present in the system in the amount required to achieve a clear uniform blend.

A preferred plasticizer/solvent system for use with a polyamide resin, such as Unirez 2931, comprises a mixture of about 18.1 weight percent Santicizer 8, 35.2 weight percent mineral oil titrated to clarity with 46.7 weight percent Igepal C0210. This system has a solubility parameter of 9.2 which is compatible with the polyamide solubility parameter of about 9 to 12.5.

In the composition of the invention, for each part of the plasticizer 6 to 10 parts, most preferably 7 to 9 parts, by weight of polyamide are employed. Twelve to twenty parts, most preferably 13 to 18 parts, by weight polyamide are employed for each part mineral oil. If excessive amounts of gellant are used, the set point may be elevated, thus requiring elevated processing temperatures and the potential for greater fragrance loss. Too little gellant may result in a composition which is too soft. Plasticizer levels below the recommended levels may result in compositions, the high viscosity of which, leads to processing difficulty. In general, of course, the amounts of plasticizer, gellant and cosolvent must also be such as to create a solubility parameter compatible with the polyamide being employed.

The plasticizer/solvent system and polyamide resin are blended at a temperature at which they are fluid. With the preferred materials temperatures of about 120° to 146° C. are sufficient. Following mixing to a homogeneous composition, the temperature of the composition is reduced to about 120° C. or less. However, the temperature of the composition at this stage is maintained above its set point. Warmed fragrance oil is then added to the composition to yield the composition of the invention. Up to 15 weight percent of the compositon may be fragrance oil. All types of fragrance oils with a variety of scent types may be employed. Coloring agents stabilizers or any other desired ingredient such as glitter, pearlizing agents, etc. may optionally be employed in the invention and may be added with the fragrance oil. Materials soluble in the fragrance, such as oil soluble dyes, are suitable for use in the composition of the invention.

The composition of the invention, when homogeneously blended, may be molded into any chosen shape, including three dimensional articles. Rotational molding may be utilized given the composition's relatively low set point and reduced potential for fragrance loss. Hollow and solid casting techniques may also be used. The compositions have flow and coating properties which facilitate the molding operation.

The product which is formed is rigid and retains its form with age. The articles are clear and discoloration caused by fragrance exposure to elevated temperatures is not observed with a properly chosen fragrance. During storage, both wrapped and unwrapped, and in use synersis is avoided. The surface of the articles does not become tacky and in use good fragrance lift is effected.

The following example is illustrative of the invention. In all cases in this application references to percentages or parts refer to weight percent or parts by weight unless the context clearly indicates a different meaning.

EXAMPLE

Transparent fragrance-emitting articles were formed from the compositions listed in Table 1 below.

TABLE 1

| Component | I | II |
|---|---|---|
| Polyamide Resin Unirez 2931 | 59.997 | 64.997 |
| Light mineral oil | 8.800 | 7.038 |
| Santicizer 8 | 4.600 | 3.63 |
| Igepal CO 210 | 11.600 | 9.332 |
| Fragrance oil | 15.000 | 15.0 |
| Colorants | 0.003 | 0.003 |

The polyamide resin and the plasticizer/solvent system were blended together in a sigma blade mixer at 140°–150° C. until uniform. The mixture was cooled to 120° C. and fragrance oil, warmed to 80°–100° C., was mixed into the above mixture until the system was homogeneous. The mixture was maintained at 110°–120° C. for about an hour and cast into molds.

After cooling, the molded articles were hard and tack-free with both good fragrance diffusion and stability. The articles retained these properties (both wrapped and unwrapped) even after being subjected to accelerated aging including high humidity exposure (90% RH/100° F.) for one month.

We claim:

1. A composition for forming a solid transparent fragrance-emitting article comprising an admixture of
   (a) 60 to 65 weight percent of a thermoplastic polyamide resin, having an average molecular weight of 5,000 to 15,000 which is formed by reaction of a polycarboxylic acid of the formula R(COOH)x wherein R is a hydrocarbon group having 20 to 44 carbon s and x is 2 or more, with a polyamine;
   (b) said resin being homogeneously blended with 20 to 30 weight percent of a clear plasticizer/solvent system comprising a sulfonamide plasticizer, a gellant and a cosolvent for the plasticizer and the gellant, the solubility parameter of the polyamide resin and plasticizer system being compatible; and
   (c) up to 15 weight percent of a fragrance oil, said composition being clear, homogeneous, and fluid at a temperature below 120° C.

2. The composition of claim 1 wherein the polyamide resin is formed from linoleic acid dimer.

3. The composition of claim 1 wherein the polyamine is an ethylene polyamine.

4. The composition of claim 1 wherein the polyamine is diethylenetriamine.

5. The composition of claim 1 wherein the gellant is mineral oil.

6. The composition of claim 1 wherein the plasticizer is N-ethyl,o-,p-toluene sulphonamide.

7. The composition of claim 1 wherein the cosolvent is a long chain alkyl phenol ethoxylate the alkyl chain having 9 to 18 carbons and the degree of ethoxylation being 1 to 3 moles of ethylene oxide.

8. The composition of claim 1 wherein the cosolvent is nonyl phenol ethoxylate.

9. The composition of claim 1 wherein 7 to 9 parts by weight polyamide resin are used for each part by weight of plasticizer.

10. The composition of claim 1 wherein 13 to 18 parts by weight polyamide resin are used for each part by weight of gellant.

11. The composition of claim 1 wherein 2 parts by weight of gellant are used for each part by weight of plasticizer.

12. The composition of claim 1 comprising:
   (a) 60–65 weight percent polyamide resin having an average molecular weight of 8,000–12,000 formed by reaction of linoleic acid dimer and diethylene triamine;
   (b) 20 to 30 weight percent a clear plasticizer/solvent system comprising 1 part by weight N-ethyl,o-,p-toluene sulfonamide, 2 parts by weight mineral oil and nonyl phenol ethoxylate (1.5 moles EO) in an amount sufficient to make the system clear; and
   (c) a fragrance oil in an amount equal to no more than 15 weight percent of the composition.

13. A transparent fragrance-emitting article comprising a solid gel formed by
   (a) admixing until homogeneous at a temperature at which the mixture is fluid
      (i) 60 to 65 parts by weight of a polyamine resin, which has an average molecular weight of 5,000 to 15,000 and is formed by reaction of a polycarboxylic acid of the formula R(COOH)x wherein R is a hydrocarbon group having 20 to 44 carbons and x is 2 or more, with a polyanide, and
      (ii) 20 to 30 parts by weight of a plasticizer/solvent system comprising 2 parts by weight of a gellant, 1 part by weight of a sulfonamide plasticizer and sufficient cosolvent for the gellant and plasticizer to render the plasticizer/solvent system clear;
   (b) cooling the admixture of resin and plasticizer/solvent system admixture to a temperature above the admixture's set point, but below about 120° C.;
   (c) adding up to 15 weight percent of fragrance oil to the cooled admixture; and
   (d) molding the resulting product.

14. The article of claim 13 wherein the polyamide resin and the plasticizer/solvent system are admixed at a temperature of about 120° C. to 146° C.

15. The article of claim 13 wherein the product is molded by rotational molding.

16. The article of claim 13 wherein the product is shell molded.

17. A method for forming a solid transparent fragrance-emitting article, while minimizing fragrance losses, comprising:
- (a) mixing until homogenous at a temperature at which the mixture is fluid
  - (i) 60 to 65 parts by weight of a thermoplastic polyamide resin, having an average molecular weight of 5,000 to 15,000 which is formed by reaction of a polycarboxylic acid of the formula $R(COOH)_x$ wherein R is a hydrocarbon group having 20 to 44 carbons and x is 2 or more, with a polyamine,
  - (ii) with 20 to 30 parts by weight of a clear plasticizer/solvent system comprising a sulfonamide plasticizer, a gellant and a cosolvent for the plasticizer and the gellant, the solubility parameter of the polyamide resin and plasticizer system being compatible; and
- (b) cooling the homogeneous mixture to a temperature below 120° C. but above the mixture's set point
- (c) adding up to 15 weight percent of warmed fragrance oil to the cooled mixture and blending until homogeneous; and
- (d) molding the resultant homogeneous blend.

* * * * *